(12) United States Patent
Nishijima (10) Patent No.: US 8,925,370 B2
(45) Date of Patent: Jan. 6, 2015

(54) PARTICULATE MATTER DETECTING APPARATUS FOR INTERNAL COMBUSTION ENGINE

(75) Inventor: Hiroki Nishijima, Suntou-gun (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 293 days.

(21) Appl. No.: 13/515,669

(22) PCT Filed: Nov. 8, 2010

(86) PCT No.: PCT/JP2010/069824
§ 371 (c)(1),
(2), (4) Date: Jun. 13, 2012

(87) PCT Pub. No.: WO2012/063303
PCT Pub. Date: May 18, 2012

(65) Prior Publication Data
US 2012/0247181 A1  Oct. 4, 2012

(51) Int. Cl.
*G01N 37/00* (2006.01)
*G01N 15/06* (2006.01)

(52) U.S. Cl.
CPC ........ *G01N 15/0656* (2013.01); *F01N 2560/05* (2013.01)
USPC ....................................... 73/28.01

(58) Field of Classification Search
CPC ...................... G01N 15/0656; G01N 15/06
USPC ................... 73/28.01, 23.31, 28.02
See application file for complete search history.

(56) References Cited

U.S. PATENT DOCUMENTS

| | | | |
|---|---|---|---|
| 7,364,606 B2 * | 4/2008 | Shimoda et al. | 96/18 |
| 2006/0249024 A1 * | 11/2006 | Shimoda et al. | 96/19 |
| 2008/0105567 A1 | 5/2008 | Okayama et al. | |
| 2009/0051376 A1 | 2/2009 | Schnell et al. | |
| 2010/0072055 A1 * | 3/2010 | Tanaka et al. | 204/164 |
| 2010/0206167 A1 | 8/2010 | Okayama et al. | |

FOREIGN PATENT DOCUMENTS

| | | |
|---|---|---|
| CN | 1969179 | 5/2007 |
| EP | 2 202 509 A1 | 6/2010 |
| JP | 2008-502892 A | 1/2008 |
| JP | 2008-139294 A | 6/2008 |
| JP | 2009-144577 A | 7/2009 |
| JP | 2010-151553 A | 7/2010 |
| JP | 2010-151554 A | 7/2010 |
| JP | 2010-190615 A | 9/2010 |

* cited by examiner

*Primary Examiner* — Hezron E Williams
*Assistant Examiner* — Rodney T Frank
(74) *Attorney, Agent, or Firm* — Sughrue Mion, PLLC (57) ABSTRACT

An object of the present invention is to provide a particulate matter detecting apparatus for an internal combustion engine that can maintain an appropriate balance between reduction in time required for one detecting sequence and limiting of power consumption of a heater for sensor reset.
The particulate matter detecting apparatus for an internal combustion engine includes: a sensor disposed at an exhaust passage of an internal combustion engine, the sensor including a pair of electrodes for trapping particulate matter; voltage applying means for applying voltage across the electrodes; discharge amount index acquiring means for acquiring a predetermined index associated with a discharge amount of the particulate matter; and voltage adjusting means for adjusting the voltage to be applied across the electrodes based on the index acquired by the discharge amount index acquiring means such that the voltage is lower when the discharge amount is large than when the discharge amount is small.

5 Claims, 6 Drawing Sheets

PARTICULATE MATTER DETECTING APPARATUS FOR INTERNAL COMBUSTION ENGINE

CROSS REFERENCE TO RELATED APPLICATION

This application is a National Stage of International Application No. PCT/JP2010/069824 filed Nov. 8, 2010, the contents of all of which are incorporated herein by reference in their entirety.

TECHNICAL FIELD

The present invention relates to a particulate matter detecting apparatus for an internal combustion engine.

BACKGROUND ART

JP-A-2009-144577 discloses an apparatus for determining failure of a particulate filter. This apparatus includes a particulate filter, an electric insulating material, a plurality of electrodes, and control means. More specifically, the particulate filter is disposed at an exhaust passage of an internal combustion engine. The electric insulating material is disposed downstream of the particulate filter and deposited with particulate matter (PM). The electrodes are disposed, mutually spaced apart from each other, on the electric insulating material. The control means measures an index correlated with an electric resistance value across the electrodes and, when detecting that the measured index is smaller than a predetermined reference value, determines that the particulate filter is faulty.

PRIOR ART DOCUMENTS

Patent Document

Patent Document 1: JP-A-2009-144577

SUMMARY OF THE INVENTION

Problem to be Solved by the Invention

With a PM sensor as disclosed in the abovementioned patent document, voltage is applied across the electrodes to thereby generate an electric field, so that the charged particulate matter in an exhaust gas is attracted by the electric field for trapping. The particulate matter deposited between the electrodes reduces electric resistance across the electrodes, which is used for detection of an amount of particulate matter contained in the exhaust gas. The PM sensor includes a heater for burning to remove the particulate matter deposited. When the amount of particulate matter deposited on the PM sensor reaches a predetermined value, the heater is energized and the particulate matter deposited is thereby burned and removed, which resets the PM sensor.

In such a PM sensor, no change develops in the electric resistance between the electrodes after the reset until the amount of particulate matter deposited between the electrodes reaches a certain value. Time it takes the change in the electric resistance (sensor output) between the electrodes to develop after the reset of the PM sensor will hereinafter be called "dead zone time." At least time more than the dead zone time is required before one detecting sequence is completed.

An amount of particulate matter discharged per unit time varies greatly depending on, for example, operating conditions of the internal combustion engine. For example, a small amount of particulate matter discharged results from mild fluctuations in engine load, while a large amount of particulate matter discharged results from sharp fluctuations in the engine load. When the amount of particulate matter discharged per unit time remains small, it takes a longer time for the amount of particulate matter deposited between the electrodes to reach the certain value, which results in a longer dead zone time. As a result, one detecting sequence requires a longer time and a condition in which the amount of particulate matter discharged cannot be identified extends over a longer period of time, which is not desirable. In contrast, when the amount of particulate matter discharged per unit time is large, the amount of particulate matter deposited between the electrodes reaches a value that requires the reset within a short period of time. The PM sensor is thus frequently reset, which poses a problem of an increased power consumption of the heater.

The present invention has been made in view of the foregoing and it is an object of the present invention to provide a particulate matter detecting apparatus for an internal combustion engine that can maintain an appropriate balance between reduction in time required for one detecting sequence and limiting of power consumption of a heater for sensor reset.

Solution to Problem

First aspect of the present invention is an apparatus for detecting particulate matter for an internal combustion engine, comprising:

a sensor disposed at an exhaust passage of an internal combustion engine, the sensor including a pair of electrodes for trapping particulate matter;

voltage applying means for applying voltage across the electrodes;

discharge amount index acquiring means for acquiring a predetermined index associated with a discharge amount of the particulate matter; and voltage adjusting means for adjusting the voltage to be applied across the electrodes based on the index acquired by the discharge amount index acquiring means such that the voltage is lower when the discharge amount is large than when the discharge amount is small.

Second aspect of the present invention is the apparatus for detecting particulate matter for an internal combustion engine according to the first aspect, wherein:

the index includes a value representing severity with which load of the internal combustion engine fluctuates.

Third aspect of the present invention is the apparatus for detecting particulate matter for an internal combustion engine according to the first aspect, wherein:

the index includes a time that elapses before a change appears in an output of the sensor after particulate matter deposited on the sensor is removed.

Fourth aspect of the present invention is the apparatus for detecting particulate matter for an internal combustion engine according to any one of the first to the third aspects, comprising:

average operating time calculating means for calculating an average operating time that represents an average operating time of the internal combustion engine per trip; and correcting means for correcting the voltage to be applied across the electrodes such that the voltage is greater when the average operating time calculated by the average operating time calculating means is short than when the average operating time is long.

Effects of the Invention

In the first aspect of the present invention, when the particulate matter discharge amount is large, the applied voltage across the electrodes is made to be relatively low to thereby weaken the electric field. This allows a pace at which the particulate matter deposits between the electrodes to be limited. This allows a situation, in which a sensor reset for removing the particulate matter deposited between the electrodes occurs frequently, to be reliably prevented from occurring even when the particulate matter discharge amount is large. The power consumption of the heater required for the sensor reset can therefore be reduced. In contrast, when the particulate matter discharge amount is small, the electric field can be intensified by setting the applied voltage across the electrodes to a relatively high value. This allows the pace at which the particulate matter deposits between the electrodes to be increased, so that time required for one sequence of detecting the particulate matter can be shortened. As a result, the time required for one sequence of detection can be prevented from becoming too long even when the particulate matter discharge amount is small.

In the second aspect of the present invention, the index is a value representing severity with which load of the internal combustion engine fluctuates. The particulate matter discharge amount, whether it is large or small, can therefore be accurately estimated.

In the third aspect of the present invention, the index is a time (a dead zone time) that elapses before a change appears in the output of the sensor after the particulate matter deposited on the sensor is removed. The particulate matter discharge amount, whether it is large or small, can therefore be accurately estimated.

In the fourth aspect of the present invention, the applied voltage across the electrodes can be corrected to be greater when the average operating time of the internal combustion engine is short than when the average operating time is long. Even with the internal combustion engine used under an operating condition of a short operating time per trip, at least one sequence of detecting the particulate matter discharge amount can be properly completed before an engine stop.

MODES FOR CARRYING OUT THE INVENTION

Embodiments of the present invention will be described below with reference to the accompanying drawings. In the drawings, like or corresponding parts are identified by the same reference numerals and descriptions for those parts will be omitted.

First Embodiment

Figure 1:
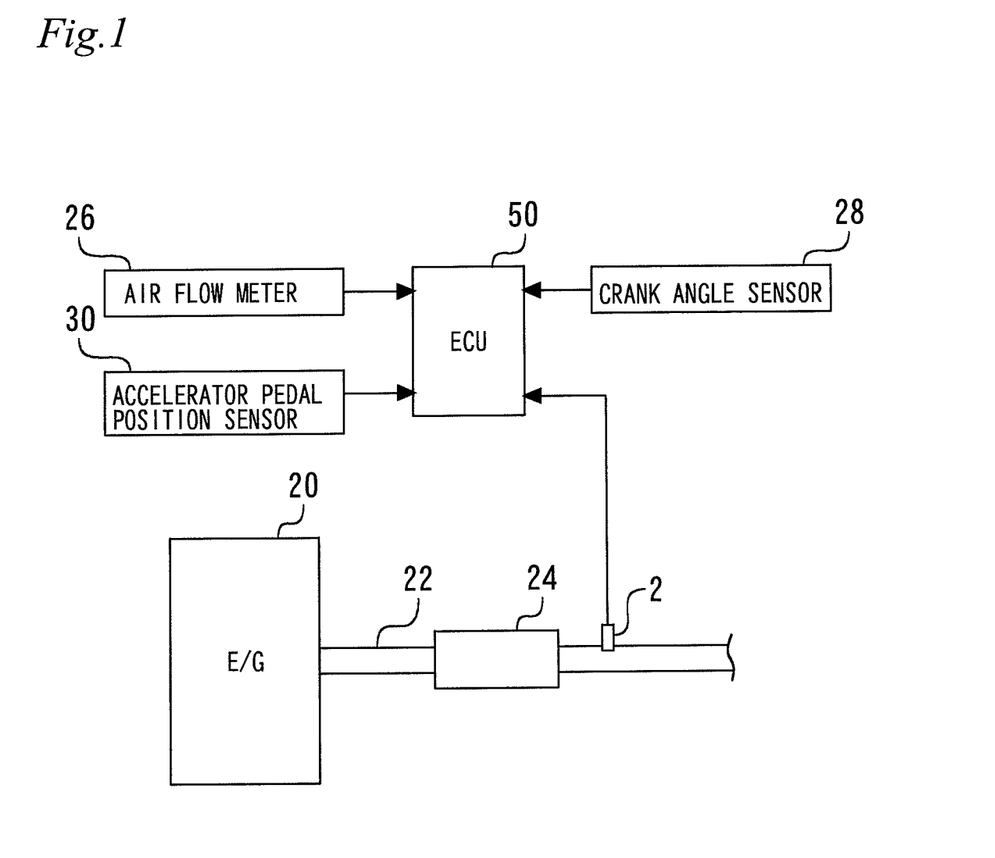
FIG. 1 is a diagram for illustrating a configuration of a system according to a first embodiment of the present invention.

FIG. 1 is a diagram for illustrating a configuration of a system according to a first embodiment of the present invention. Referring to FIG. 1, the system of this embodiment includes an internal combustion engine 20. The internal combustion engine 20 is mounted as a driving power source on, for example, a vehicle. A particulate filter 24 having a function of trapping particulate matter (hereinafter may be abbreviated to a "PM") contained in an exhaust gas is disposed midway along an exhaust passage 22 of the internal combustion engine 20. A PM sensor 2 that can detect the particulate matter is disposed on the exhaust passage 22 downstream of the particulate filter 24.

The system of this embodiment further includes an electronic control unit (ECU) 50. In addition to the PM sensor 2, various types of other engine control sensors including an air flow meter 26, a crank angle sensor 28, and an accelerator pedal position sensor 30, and various types of engine control actuators including a fuel injector, not shown, are electrically connected to the ECU 50. Specifically, the air flow meter 26 detects an intake air amount of the internal combustion engine 20. The crank angle sensor 28 detects a rotational angle of an output shaft of the internal combustion engine 20. The accelerator pedal position sensor 30 detects a depression amount of an accelerator pedal (hereinafter referred to as an "accelerator pedal position") on a driver's seat of the vehicle on which the internal combustion engine 20 is mounted.

In this embodiment, the PM sensor 2 is disposed downstream of the particulate filter 24, which allows an amount of PM discharged to the downstream side of the particulate filter 24 to be detected. If the particulate filter 24 becomes faulty, a reduced PM removal rate of the particulate filter 24 results, so that the amount of PM discharged to the downstream side of the particulate filter 24 increases greatly. In this embodiment, whether the particulate filter 24 is faulty can be accurately detected based on the amount of PM discharged to the downstream side of the particulate filter 24 as detected by the PM sensor 2.

Note, however, that the position at which to dispose the PM sensor 2 in the present invention is not limited only to the downstream side of the particulate filter 24. The PM sensor 2 may be disposed, for example, at a position at which the PM discharged from the internal combustion engine 20 is directly detected.

Figure 2:
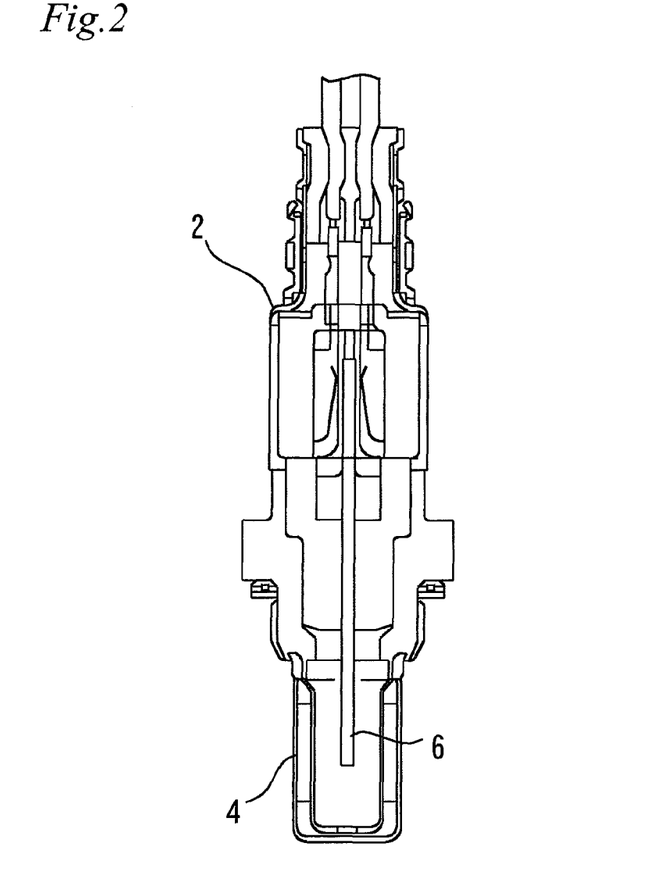
FIG. 2 is a cross-sectional view showing a PM sensor.
Figure 3:
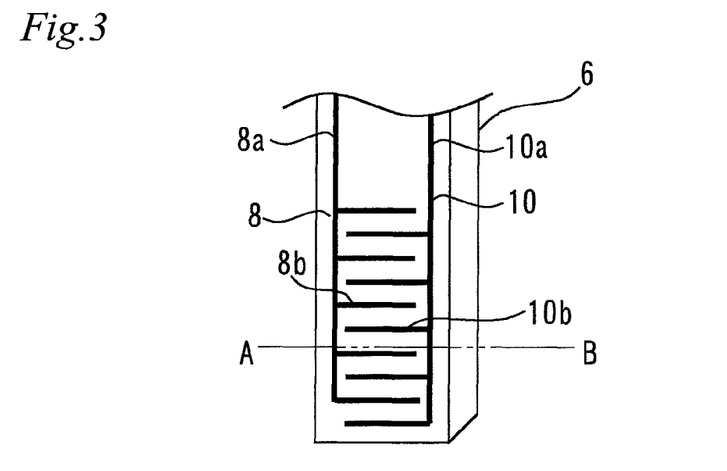
FIG. 3 is an enlarged view showing part of a sensor element section of the PM sensor.

FIG. 2 is a cross-sectional view showing the PM sensor 2. FIG. 3 is an enlarged view showing part of a sensor element section of the PM sensor 2. Referring to FIG. 2, the PM sensor 2 includes a cover 4 and an element section 6 disposed in a space inside the cover 4. The cover 4 has a plurality of holes through which gas passes. The exhaust gas flows through the multiple holes into an inside of the cover 4, so that the element section 6 is in contact with the exhaust gas.

Referring to FIG. 3, the element section 6 includes a pair of electrodes 8, 10 disposed on a surface thereof. The electrodes 8, 10 are disposed in a condition of not in contact with each other, being spaced apart from each other. Each of the electrodes 8, 10 includes a dense area in which electrodes are densely disposed as compared with other parts. More specifically, the electrodes 8, 10 include conductive parts 8a, 10a, respectively, at the other area of the dense area, the conductive parts 8a, 10a extending in a longitudinal direction of the element section 6. The dense areas near a leading end of the element section 6 include the conductive parts 8a, 10a and a plurality of conductive parts 8b, 10b formed in a direction extending perpendicularly to the conductive parts 8a, 10a. Specifically, the electrodes 8, 10 include the conductive parts 8b, 10b, respectively, each of the conductive parts 8b, 10b being arranged in a comb-like structure at the dense area of the element section 6, the comb-like structures being interdigitated with each other.

Figure 4:
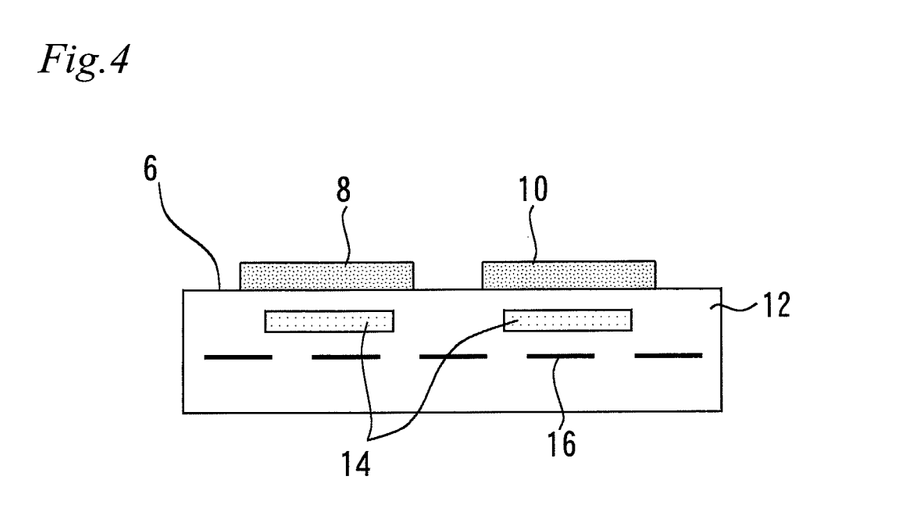
FIG. 4 is a schematic cross-sectional view taken along line A-B in FIG. 3.
Figure 5:
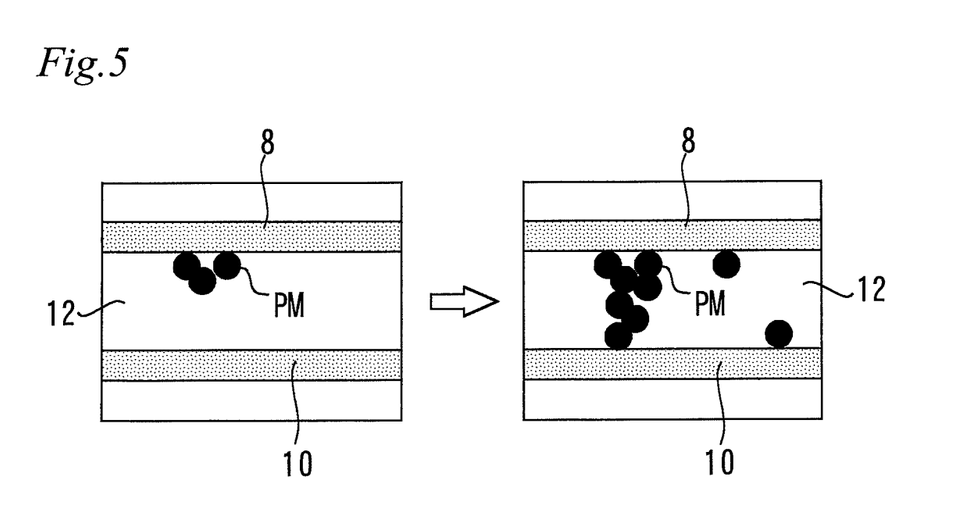
FIG. 5 illustrates schematically how PM is deposited between electrodes.

FIG. 4 is a schematic cross-sectional view taken along line A-B in FIG. 3. The upper side in FIG. 4 corresponds to a front surface side of the element section 6 in FIG. 3. FIG. 5 illustrates schematically how the PM is deposited between the electrodes 8, 10.

Referring to FIG. 4, the electrodes 8, 10 are disposed in contact with an insulating layer 12. The insulating layer 12 has a function of making the PM stick thereto. Temperature sensors 14 (temperature detecting means), such as a thermocouple, are embedded in the insulating layer 12 at positions near the electrodes 8, 10 to be associated therewith.

Each of the electrodes 8, 10 is connected via, for example, a power circuit to a power source (not shown). This allows voltage to be applied across the electrodes 8, 10. The application of the voltage generates an electric field between the electrodes 8, 10. The electric field attracts the PM charged in the exhaust gas to thereby let the PM deposit between the electrodes 8, 10 (see FIG. 5).

Each of the temperature sensors 14 is connected via a predetermined circuit to a detector (not shown) for detecting an electromotive force generated therein. The detection of the electromotive force of the temperature sensors 14 allows temperatures near the electrodes 8, 10 to be detected.

A heater 16 (heating means) is embedded in a layer beneath the temperature sensors 14. The heater 16 is formed such that a heat center thereof is disposed in a layer immediately below the dense areas of the electrodes 8, 10 to thereby ensure that the dense areas are specifically heated efficiently. The heater 16 is energized through, for example, a power circuit.

The detector, the power circuit, and the like are electrically connected to, and controlled by, the ECU 50. The PM sensor 2 outputs a sensor output that corresponds to the electric resistance across the electrodes 8, 10. The ECU 50 can detect the amount of PM discharged (an amount of PM that has passed the position at which the PM sensor 2 is disposed) based on the sensor output from the PM sensor 2.

When the amount of PM deposited between the electrodes 8, 10 exceeds a predetermined limit, the PM deposited needs to be removed. According to this embodiment, energizing the heater 16 to thereby heat the element section 6 allows the amount of PM deposited between the electrodes 8, 10 to be burned and removed. Energization of the heater 16 to thereby remove the PM deposited between the electrodes 8, 10 is referred to as a "reset."

Figure 6:
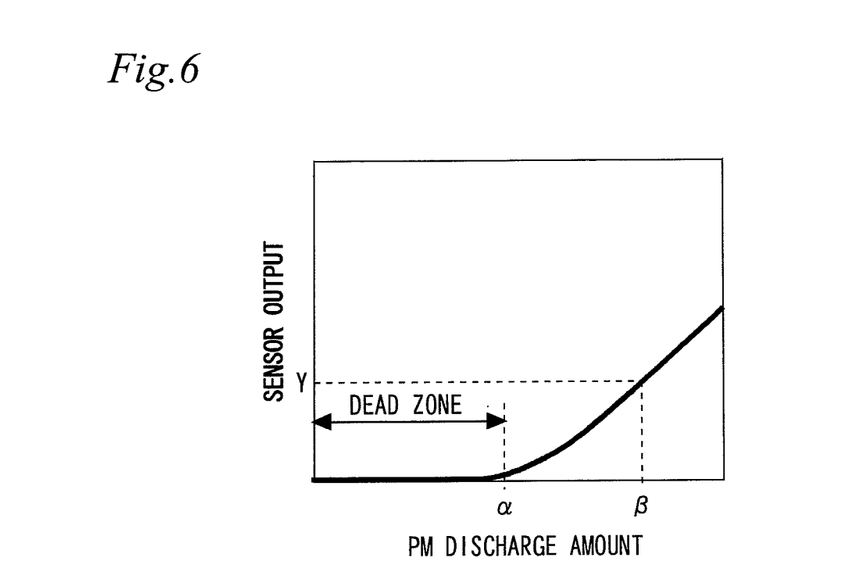
FIG. 6 is a graph showing a relationship between a sensor output of the PM sensor and an amount of PM discharged.

Detection of the amount of PM discharged is started in a condition in which the PM sensor 2 is reset. FIG. 6 is a graph showing a relationship between the sensor output of the PM sensor 2 when the amount of PM discharged is detected and the amount of PM discharged. The amount of PM discharged represented by the abscissa of FIG. 6 is a total amount of PM that has passed the position at which the PM sensor 2 is disposed after the reset.

A path across the electrodes 8, 10 is insulated when the PM sensor 2 is in a reset condition. The sensor output is zero when the path across the electrodes 8, 10 is insulated. The sensor output is therefore zero in the beginnings of a detection sequence as shown in FIG. 6. The left illustration of FIG. 5 shows a condition in which, although the PM starts to deposit between the electrodes 8, 10, a conductive path is yet to be formed. In this condition, the path across the electrodes 8, 10 remains insulated, so that the sensor output remains zero. When the PM further deposits between the electrodes 8, 10 and the amount of PM deposited reaches a certain level, the PM deposited forms a conductive path between the electrodes 8, 10 as shown in the right illustration of FIG. 5. Formation of such a conductive path reduces the electric resistance across the electrodes 8, 10, which lets the sensor output start increasing from zero. As the amount of PM deposited further increases, the conductive path becomes larger, so that the electric resistance across the electrodes 8, 10 decreases further. Thus, the sensor output increases with a decreasing electric resistance across the electrodes 8, 10.

The electric field generated by the application of the voltage across the electrodes 8, 10 causes the PM contained in the exhaust gas that flows past the position at which the PM sensor 2 is disposed to be attracted by the PM sensor 2 at a certain rate and deposited between the electrodes 8, 10. As a result, there is a correlation between the amount of PM that has passed the position at which the PM sensor 2 is disposed (PM discharge amount) and the amount of PM deposited between the electrodes 8, 10. Further, there is the relationship mentioned earlier between the amount of PM deposited between the electrodes 8, 10 and the sensor output. Specifically, when the amount of PM deposited between the electrodes 8, 10 reaches the certain level, a conductive path is formed and the sensor output starts increasing from zero. When the amount of PM deposited further increases, the sensor output increases further. Hence a relationship between the sensor output and the PM discharge amount is as shown in FIG. 6. The PM discharge amount can therefore be found based on the sensor output.

Referring to FIG. 6, the PM discharge amount when the sensor output starts increasing from zero (when the conductive path is formed) is a certain value a (e.g. 30 mg). This therefore allows the ECU 50 to determine that, after the PM sensor 2 is reset and the detection sequence is started, the PM discharge amount for a period from the reset to a particular point in time at which the sensor output starts increasing from zero reaches the above value α. Alternatively, an arrangement may be made in which the ECU 50 determines that the PM discharge amount for a period from the reset to a particular point in time at which the sensor output is Y reaches β as shown in FIG. 6.

Additionally, the ECU 50 determines whether the amount of PM deposited between the electrodes 8, 10 reaches a level at which a reset is required based on, for example, the sensor output. If determining that the amount of PM deposited reaches the level at which a reset is required, the ECU 50 resets the PM sensor 2. When the reset of the PM sensor 2 is completed, the next sequence of detecting the PM discharge amount is started.

In the description that follows, the PM discharge amount when the sensor output starts increasing from zero is referred to as a "detection lower limit PM amount." As shown in FIG. 6, the sensor output remains zero for a period of time until the PM discharge amount reaches the detection lower limit PM amount a after the reset. A range over which the PM discharge amount is less than the detection lower limit PM amount a is a dead zone in which the sensor output does not respond to the PM discharge amount. Therefore, the sensor output remains zero for the period of time until the PM discharge amount reaches the detection lower limit PM amount a after the reset, so that the PM discharge amount cannot be detected during this period.

A period of time until the sensor output starts increasing from zero after the reset will be hereinafter referred to as "dead zone time." Specifically, the dead zone time is a period of time over which the PM discharge amount reaches the detection lower limit PM amount α after the reset. When the PM discharge amount per unit time is large, the PM discharge amount reaches the detection lower limit PM amount α within a short period of time after the reset, which results in a shorter dead zone time. In contrast, when the PM discharge amount per unit time is small, it takes a long time for the PM discharge amount to reach the detection lower limit PM amount a after the reset, which results in a longer dead zone time.

The amount of PM discharged from the internal combustion engine 20 per unit time varies greatly depending on the operating condition of the internal combustion engine 20, greatly depending on the manner of driving by a driver of the vehicle. For example, a driver who tends to accelerate suddenly and operate the accelerator pedal frequently subjects engine load to many sudden fluctuations, causing the PM discharge amount per unit time to increase. On the other hand, a driver who develops a habit of driving mildly with restrained numbers of sudden accelerations and accelerator pedal operations yields mild fluctuations in engine load, so that the PM discharge amount per unit time decreases. The particulate filter 24 generally traps the PM in the exhaust gas at a certain rate. As a result, the amount of PM discharged from the internal combustion engine 20 per unit time and the PM discharge amount per unit time downstream of the particulate filter 24 exhibit a similar tendency.

From the foregoing, when the amount of PM discharged from the internal combustion engine 20 per unit time is small, it takes a long time for the PM discharge amount to reach the detection lower limit PM amount a after the reset of the PM sensor 2, which results in a longer dead zone time. If the dead zone time is too long, time required for one detection sequence is long, so that a condition in which the ECU 50 is unable to determine the PM discharge amount extends over a long time. This situation is not desirable, since the particulate filter 24, if developing a fault, may not be detected immediately.

In contrast, if the amount of PM discharged from the internal combustion engine 20 per unit time is large, the PM deposits between the electrodes 8, 10 at a rapid pace, so that the amount of PM deposited between the electrodes 8, 10 reaches the level at which a reset is required within a short period of time. This results in the PM sensor 2 being reset frequently, which poses a problem of an increased power consumption by the heater 16.

Figure 7:
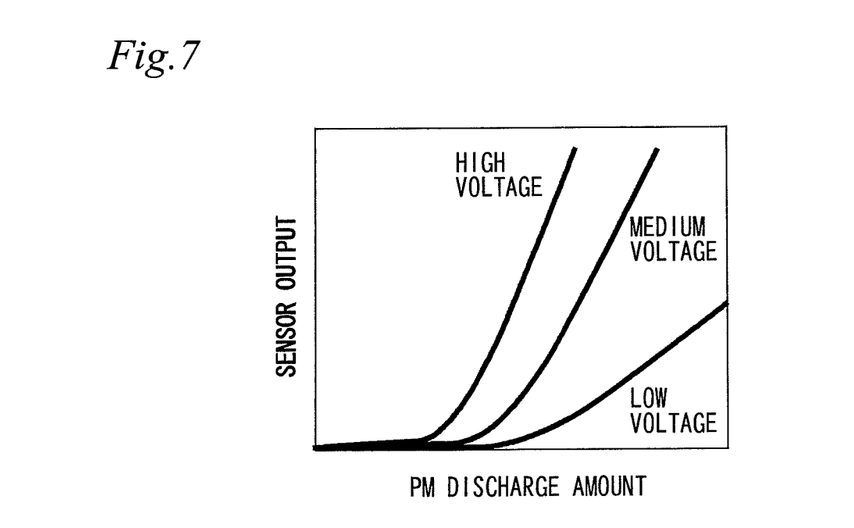
FIG. 7 is a graph showing relationships between a sensor output of the PM sensor and an amount of PM discharged.

To solve the foregoing problems, desirably, the PM discharge amount, whether it is large or small, is estimated and, according to the result of the estimation, the applied voltage across the electrodes 8, 10 is varied accordingly. FIG. 7 is a graph for illustrating an effect of the applied voltage across the electrodes 8, 10. FIG. 7 shows a relationship between the sensor output of the PM sensor 2 and the PM discharge amount when the PM discharge amount is detected with different applied voltages. An increased applied voltage across the electrodes 8, 10 intensifies the electric field generated, achieving a stronger force attracting the PM in the exhaust gas. Therefore, a high applied voltage across the electrodes 8, 10 increases a ratio with which the PM in the exhaust gas deposits between the electrodes 8, 10. As a result, the higher the applied voltage across the electrodes 8, 10, the faster the pace at which the amount of PM deposited between the electrodes 8, 10 increases, so that the conductive path is formed at early timing. Consequently, the higher the applied voltage across the electrodes 8, 10, the shorter the dead zone time and the smaller the detection lower limit PM amount α.

If the applied voltage across the electrodes 8, 10 is low, on the other hand, the electric field generated is weak, so that the force attracting the PM in the exhaust gas is weak. The ratio with which the PM in the exhaust gas deposits between the electrodes 8, 10 is thus small. Consequently, with a low applied voltage across the electrodes 8, 10, the pace at which the amount of PM deposited between the electrodes 8, 10 increases is slow, which extends the dead zone time and increases the detection lower limit PM amount α.

In view of the foregoing, in this embodiment, the applied voltage across the electrodes 8, 10 is made relatively high when the PM discharge amount is estimated to be small. This allows the dead zone time to be shortened. Even when the PM discharge amount is small, therefore, the time required for one sequence of detecting the PM discharge amount can be prevented from becoming too long. When the PM discharge amount is estimated to be large, the applied voltage across the electrodes 8, 10 is made relatively low. This allows the pace at which the amount of PM deposited between the electrodes 8, 10 increases to be reduced, so that a frequency at which the PM sensor 2 is reset can be reduced. Even when the PM discharge amount is large, therefore, the power consumption of the heater 16 can be limited.

In addition, in this embodiment, the PM discharge amount, whether it is large or small, is estimated as detailed below. Specifically, as described earlier, for the driver who tends to accelerate suddenly and operate the accelerator pedal frequently, the amount of PM discharged from the internal combustion engine 20 per unit time can be estimated to be large. A time-integrated value of a rate of change in the accelerator pedal position when the accelerator pedal position changes toward a plus direction (hereinafter referred to as an "accelerator pedal position rate-of-change integrated value") serves as an index indicating a frequency of sudden acceleration and accelerator pedal operation during the period of integration. A large accelerator pedal position rate-of-change integrated value therefore permits a determination that the sudden acceleration and accelerator pedal operation are frequently performed and the PM discharge amount is large. By contrast, a small accelerator pedal position rate-of-change integrated value permits a determination that the sudden acceleration and accelerator pedal operation are performed less frequently and the PM discharge amount is small. In this embodiment, therefore, when the accelerator pedal position rate-of-change integrated value is large, a correction is made to decrease the applied voltage across the electrodes 8, 10 and, when the accelerator pedal position rate-of-change integrated value is small, a correction is made to increase the applied voltage across the electrodes 8, 10.

Figure 8:
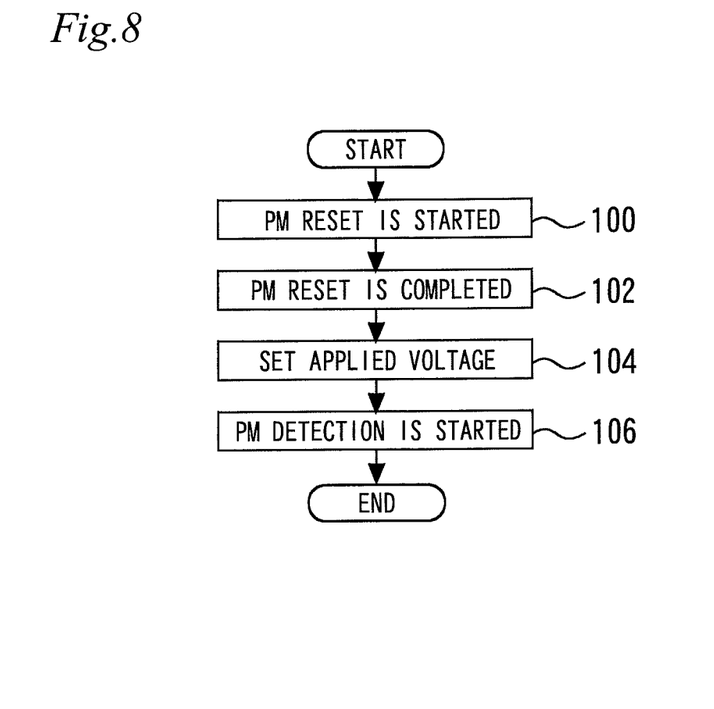
FIG. 8 is a flow chart showing a routine performed in the first embodiment of the present invention.

FIG. 8 is a flow chart showing a routine performed by the ECU 50 for detecting the PM discharge amount in this embodiment. According to the routine shown in FIG. 8, the reset of the PM sensor 2 is started first (step 100). When the PM deposited between the electrodes 8, 10 is removed, the reset of the PM sensor 2 is completed (step 102).

Figure 9:
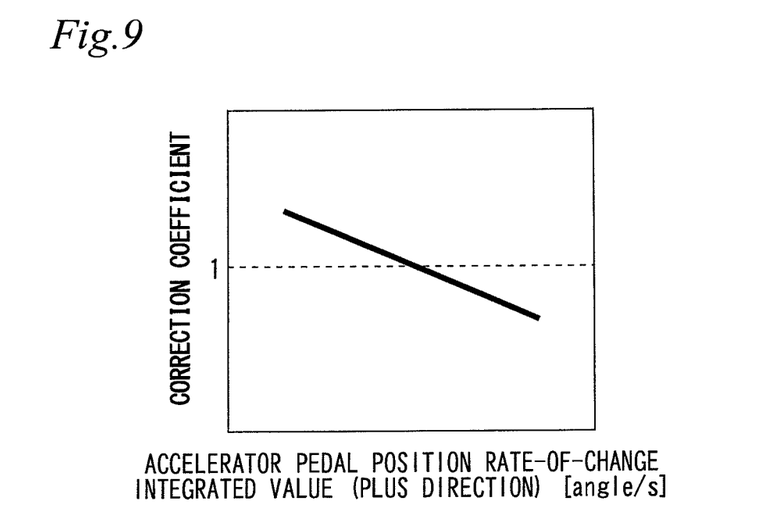
FIG. 9 is a map showing a relationship between an accelerator pedal position rate-of-change integrated value and a correction coefficient of an applied voltage.

Next, prior to the start of detection of the PM discharge amount, a process is performed to set the applied voltage across the electrodes 8, 10 (step 104). The ECU 50 calculates the accelerator pedal position rate-of-change integrated value during a past predetermined period of time sequentially based on a history of outputs of the accelerator pedal position sensor 30. As described earlier, the larger the accelerator pedal position rate-of-change integrated value, the more pronounced can the tendency be estimated toward a greater amount of PM discharged from the internal combustion engine 20 per unit time, and the smaller the accelerator pedal position rate-of-change integrated value, the more pronounced can the tendency be estimated toward a smaller amount of PM discharged from the internal combustion engine 20 per unit time. In step 104, the accelerator pedal position rate-of-change integrated value is read. FIG. 9 is a map showing a relationship between the accelerator pedal position rate-of-change integrated value and a correction coefficient of the applied voltage. The map shown in FIG. 9 is set such that the larger the accelerator pedal position rate-of-change integrated value, the smaller the correction coefficient. In step 104, a standard applied voltage is multiplied by the correction coefficient obtained based on the map of FIG. 9 to thereby find the applied voltage used for the current detection of the PM discharge amount. With the applied voltage set as described above, the detection of the PM discharge amount is started (step 106). In step 106, the voltage set in step 104 is applied across the electrodes 8, 10.

According to the processes of the routine shown in FIG. 8 as described above, when the accelerator pedal position rate-of-change integrated value is relatively small, specifically, when it is estimated that the PM discharge amount tends to be small, the correction coefficient is made large. This results in the applied voltage across the electrodes 8, 10 being higher than the standard. This allows the dead zone time to be shortened, so that the time required for one sequence of detecting the PM discharge amount can be prevented from becoming too long.

When the accelerator pedal position rate-of-change integrated value is relatively large, specifically, when it is estimated that the PM discharge amount tends to be large, the correction coefficient is made small. This results in the applied voltage across the electrodes 8, 10 being lower than the standard. This allows the frequency at which the PM sensor 2 is reset to be reduced and power consumption of the heater 16 to be limited.

The accelerator pedal position rate-of-change integrated value in the first embodiment described above corresponds to the "index" in the first and second aspects of the present invention. Similarly, the application of the voltage across the electrodes 8, 10 via, for example, the power circuit by the ECU 50 achieves the "voltage applying means" in the first aspect of the present invention, the calculation of the accelerator pedal position rate-of-change integrated value in the past predetermined period of time achieves the "discharge amount index acquiring means" in the first aspect of the present invention, and the performance of step 104 achieves the "voltage adjusting means" in the first aspect of the present invention.

Second Embodiment

A second embodiment of the present invention will be described below with reference to FIG. 10. Differences from the first embodiment described above will be mainly described and descriptions of similarities will be simplified or omitted.

In the first embodiment described above, the PM discharge amount, whether it is large or small, is estimated based on the accelerator pedal position rate-of-change integrated value. In contrast, in this embodiment, the PM discharge amount, whether it is large or small, is estimated based on a time-integrated value of a change in an air flow rate toward a plus direction as detected by the air flow meter 26 (hereinafter referred to as an "air flow rate change integrated value"). An air flow rate change integrated value that is relatively large for a certain period of time indicates that there are a number of sudden fluctuations in the engine load during that particular period of time and it can be estimated that the PM discharge amount is large during that period of time. If the air flow rate change integrated value during that particular period of time is relatively small, on the other hand, it indicates that the fluctuations in the engine load during that particular period of time are mild. This justifies estimation that the PM discharge amount is small.

Figure 10:
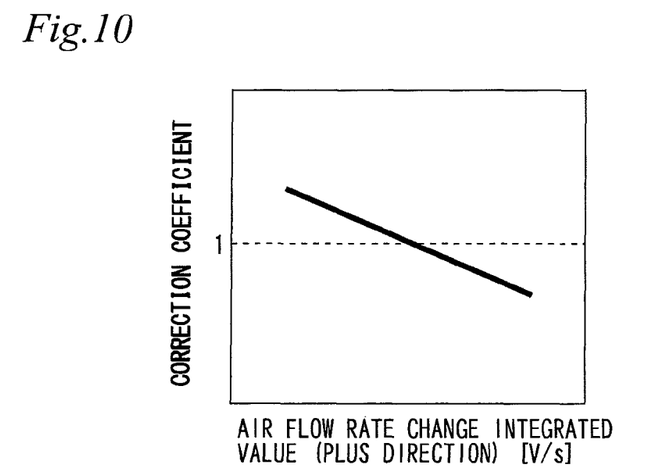
FIG. 10 is a map showing a relationship between an air flow rate change integrated value and a correction coefficient of an applied voltage.

FIG. 10 is a map showing a relationship between the air flow rate change integrated value and the correction coefficient of the applied voltage. The map shown in FIG. 10 is set such that the larger the air flow rate change integrated value, the smaller the correction coefficient. The ECU 50 calculates the air flow rate change integrated value during a past predetermined period of time sequentially based on a history of outputs of the air flow meter 26. In this embodiment, in step 104 shown in FIG. 8, the correction coefficient is found based on the map shown in FIG. 10 instead of the map shown in FIG. 9. The standard applied voltage is then multiplied by the correction coefficient thus obtained to thereby set the applied voltage across the electrodes 8, 10.

According to this embodiment, when the air flow rate change integrated value is relatively small, specifically, when it is estimated that the PM discharge amount tends to be small, the correction coefficient is made large. This results in the applied voltage across the electrodes 8, 10 being higher than the standard. This allows the dead zone time to be shortened, so that the time required for one sequence of detecting the PM discharge amount can be prevented from becoming too long.

When the air flow rate change integrated value is relatively large, specifically, when it is estimated that the PM discharge amount tends to be large, the correction coefficient is made small. This results in the applied voltage across the electrodes 8, 10 being lower than the standard. This allows the frequency at which the PM sensor 2 is reset to be reduced and power consumption of the heater 16 to be limited.

The air flow rate change integrated value in the second embodiment described above corresponds to the "index" in the first and second aspects of the present invention.

Third Embodiment

A third embodiment of the present invention will be described below with reference to FIG. 11. Differences from the first embodiment described above will be mainly described and descriptions of similarities will be simplified or omitted.

In the first embodiment described above, the PM discharge amount, whether it is large or small, is estimated based on the accelerator pedal position rate-of-change integrated value. In contrast, in this embodiment, the PM discharge amount, whether it is large or small, is estimated based on the dead zone time in past sequences of detecting the PM discharge amount. If the dead zone time is short in the past sequences of detecting the PM discharge amount, the pace at which the PM is deposited between the electrodes 8, 10 is considered to be fast, so that it can be estimated that the PM discharge amount tends to be large. In contrast, if the dead zone time is long in the past sequences of detecting the PM discharge amount, the pace at which the PM is deposited between the electrodes 8, 10 is considered to be slow, so that it can be estimated that the PM discharge amount tends to be small.

Figure 11:
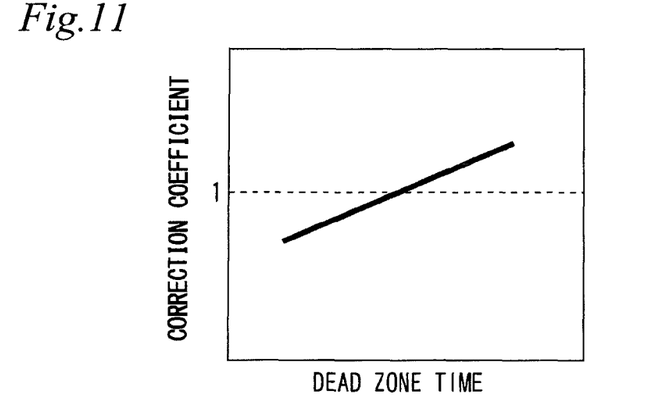
FIG. 11 is a map showing a relationship between a dead zone time and a correction coefficient of an applied voltage.

FIG. 11 is a map showing a relationship between the dead zone time and the correction coefficient of the applied voltage. The map shown in FIG. 11 is set such that the longer the dead zone time, the larger the correction coefficient. The ECU 50 calculates an indicative dead zone time in the past sequences of detecting the PM discharge amount (e.g. an average value in a predetermined number of detection sequences performed in the past). In this embodiment, in step 104 shown in FIG. 8, the correction coefficient is found based on the map shown in FIG. 11 instead of the map shown in FIG. 9. The standard applied voltage is then multiplied by the correction coefficient thus obtained to thereby set the applied voltage across the electrodes 8, 10.

According to this embodiment, when the dead zone time in the past sequences of detecting the PM discharge amount is relatively long, specifically, when it is estimated that the PM discharge amount tends to be small, the correction coefficient is made large. This results in the applied voltage across the electrodes 8, 10 being higher than the standard. This allows the dead zone time to be shortened, so that the time required for one sequence of detecting the PM discharge amount can be prevented from becoming too long.

When the dead zone time is relatively short, specifically, when it is estimated that the PM discharge amount tends to be large, the correction coefficient is made small. This results in the applied voltage across the electrodes 8, 10 being lower than the standard. This allows the frequency at which the PM sensor 2 is reset to be reduced and the power consumption of the heater 16 to be limited.

The dead zone time in the third embodiment described above corresponds to the "index" in the first and third aspects of the present invention.

Fourth Embodiment

A fourth embodiment of the present invention will be described below with reference to FIG. 12. Differences from the embodiments described above will be mainly described and descriptions of similarities will be simplified or omitted.

In this embodiment, control as detailed below is performed in combination with any of the first to third embodiments described above. Take, for instance, a vehicle used for purposes involving a short travel distance on average per trip. In such a vehicle, one operation period (extending from start to stop) of the internal combustion engine 20 may tend to be short. In such cases, if the dead zone time is too long relative to one operation period, it is likely that the internal combustion engine 20 will be stopped before even one sequence of detecting the PM discharge amount is completed. Such a situation, if it occurs, causes the ECU 50 to fail to identify such information as the PM discharge amount or whether the particulate filter 24 is faulty, which is undesirable.

To solve such a problem, according to this embodiment, if one operation period of the internal combustion engine 20 tends to be short, a correction is made to increase the applied voltage across the electrodes 8, 10 to thereby shorten the dead zone time. The ECU 50 learns and calculates an average operating time that represents an average operating time per trip in the past based on a history of operations of the internal combustion engine 20 in the past. For example, the average operating time is calculated by dividing a total operating time of the internal combustion engine 20 by the number of starts. FIG. 12 is a map showing a relationship between the average operating time and the correction coefficient of the applied voltage. The map shown in FIG. 12 is set such that the correction coefficient is greater at shorter average operating times. In this embodiment, in step 104 of FIG. 8, the applied voltage calculated by any one of methods of the first to third embodiments is further multiplied by the correction coefficient obtained based on the map shown in FIG. 12 to thereby arrive at a final applied voltage.

According to this embodiment, the applied voltage across the electrodes 8, 10 is corrected to be greater if the average operating time is short, which allows the dead zone time to be shortened. Therefore, even with the internal combustion engine 20 used under an operating condition of a short operating time per trip, at least one sequence of detecting the PM discharge amount can be properly completed before the engine stop. The ECU 50 can thereby reliably identify such information as the PM discharge amount or whether the particulate filter 24 is faulty.

Figure 12:
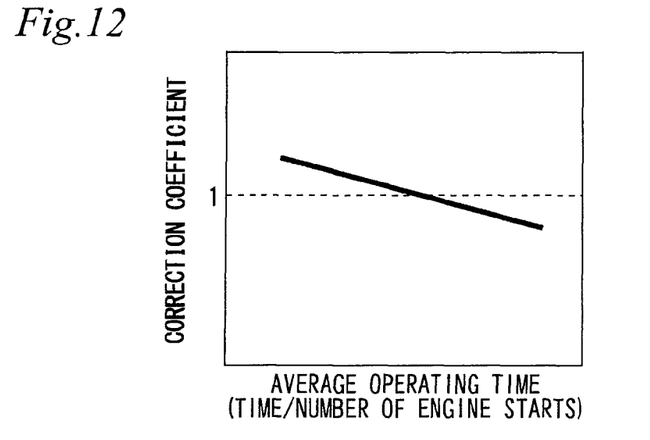
FIG. 12 is a map showing a relationship between an average operating time and a correction coefficient of an applied voltage.

In the fourth embodiment described above, the calculation of the average operating time by the ECU 50 based on the past operating history achieves the "average operating time calculating means" in the fourth aspect of the present invention and the correction of the applied voltage across the electrodes 8, 10 based on the map shown in FIG. 12 achieves the "correcting means" in the fourth aspect of the present invention.

2 PM sensor
6 element section
8, 10 electrode
12 insulating layer
14 temperature sensor
16 heater
20 internal combustion engine
22 exhaust passage
24 particulate filter
50 ECU

The invention claimed is:

1. An apparatus for detecting particulate matter for an internal combustion engine, comprising:
 a sensor disposed at an exhaust passage of an internal combustion engine, the sensor including a pair of electrodes for attracting particulate matter by an electric field between the electrodes, the sensor outputting a sensor output that corresponds to an electric resistance across the electrodes;
 voltage applying means for applying voltage across the electrodes;
 means for detecting, based on the sensor output, an amount of the particulate matter that has reached a position at which the sensor is disposed;
 discharge amount index acquiring means for acquiring an index associated with a discharge amount of the particulate matter; and
 voltage adjusting means for adjusting the voltage to be applied across the electrodes based on the index acquired by the discharge amount index acquiring means such that the voltage is lower when the discharge amount is large than when the discharge amount is small.

2. The apparatus for detecting particulate matter for an internal combustion engine according to claim 1, wherein:
 the index includes a value representing severity with which load of the internal combustion engine fluctuates.

3. The apparatus for detecting particulate matter for an internal combustion engine according to claim 1, wherein:
 the index includes a time that elapses before a change appears in an output of the sensor after particulate matter deposited on the sensor is removed.

4. The apparatus for detecting particulate matter for an internal combustion engine according to claim 1, comprising:

average operating time calculating means for calculating an average operating time that represents an average operating time of the internal combustion engine per trip; and correcting means for correcting the voltage to be applied across the electrodes such that the voltage is greater when the average operating time calculated by the average operating time calculating means is short than when the average operating time is long.

5. An apparatus for detecting particulate matter for an internal combustion engine, comprising:

a sensor disposed at an exhaust passage of an internal combustion engine, the sensor including a pair of electrodes for attracting particulate matter by an electric field between the electrodes, the sensor outputting a sensor output that corresponds to an electric resistance across the electrodes;

a voltage applying device for applying voltage across the electrodes;

a device for detecting, based on the sensor output, an amount of the particulate matter that has reached a position at which the sensor is disposed;

a discharge amount index acquiring device for acquiring an index associated with a discharge amount of the particulate matter; and a voltage adjusting device for adjusting the voltage to be applied across the electrodes based on the index acquired by the discharge amount index acquiring device such that the voltage is lower when the discharge amount is large than when the discharge amount is small.

* * * * *